United States Patent
Bahra et al.

(10) Patent No.: US 7,081,984 B1
(45) Date of Patent: Jul. 25, 2006

(54) NON-LINEAR OPTICAL DEVICES AND MATERIALS THEREFOR

(75) Inventors: Gurmit S Bahra, Sevenoaks (GB);
Penelope A Chaloner, Brighton (GB);
Lucy M Dutta, Brighton (GB);
William Healy, Sevenoaks (GB)

(73) Assignee: Qinetiq Limited, Hants (GB)

( * ) Notice: Subject to any disclaimer, the term of this patent is extended or adjusted under 35 U.S.C. 154(b) by 0 days.

(21) Appl. No.: 09/959,618

(22) PCT Filed: May 5, 2000

(86) PCT No.: PCT/GB00/01643

§ 371 (c)(1),
(2), (4) Date: Dec. 27, 2001

(87) PCT Pub. No.: WO00/68217

PCT Pub. Date: Nov. 16, 2000

(30) Foreign Application Priority Data

May 10, 1999 (GB) .................................. 9910551.2

(51) Int. Cl.
*G02F 1/355* (2006.01)
*G02F 1/37* (2006.01)

(52) U.S. Cl. .................................................. 359/328
(58) Field of Classification Search ......... 359/326–332
See application file for complete search history.

(56) References Cited

U.S. PATENT DOCUMENTS

| | | | |
|---|---|---|---|
| 3,992,366 A | * | 11/1976 | Stauner et al. ............... 530/354 |
| 5,145,610 A | | 9/1992 | Meredith et al. ............ 252/583 |
| 5,527,824 A | | 6/1996 | Scherrer ..................... 514/539 |

FOREIGN PATENT DOCUMENTS

| | | |
|---|---|---|
| EP | 0 501 656 A | 9/1992 |
| GB | 652 739 | 5/1951 |
| GB | 819 122 | 8/1959 |
| GB | 897 930 | 5/1962 |
| GB | 899 737 | 6/1962 |
| GB | 1 208 814 | 10/1970 |
| GB | 1 244 185 | 8/1971 |
| GB | 1 322 370 | 7/1973 |
| GB | 1 604 562 A | 12/1981 |
| WO | WO 91/16657 | 10/1991 |

OTHER PUBLICATIONS

Hall et al, "Polymorphism and Nonlinear Optical Activity in Organic Crystals", Journal of Crystal Growth 79 (1986) 745-751.

* cited by examiner

*Primary Examiner*—John D. Lee
(74) *Attorney, Agent, or Firm*—Nixon & Vanderhye P.C.

(57) ABSTRACT

Materials suitable for use in non-linear optical devices comprise morpholinium or thiomorpholinium salts of hydroxy-substituted aliphatic or aromatic carboxylic acids selected from tartaric acid and hydroxy-substituted benzoic and cinnamic acids, which salts have a non-centrosymmetric crystalline form. Preferred salts include morpholinium 3-hydroxybenzoate, morpholinium 4-hydroxybenzoate, morpholinium 3,5-dihydroxybenzoate, morpholinium 3-fluoro-4-hydroxybenzoate, dimorpholinium 2,3,5,6-tetrafluoro-4-hydroxybenzoate, morpholinium 4-(4-hydroxyphenyl)benzoate, morpholinium tartrate, morpholinium 4-hydroxycinnamate, thiomorpholinium 4-hydroxy-benzoate and thiomorpholinium 3,5-hydroxybenzoate.

4 Claims, No Drawings

NON-LINEAR OPTICAL DEVICES AND MATERIALS THEREFOR

This invention relates to certain novel second harmonic generator materials which produce a second harmonic generation (SHG) of optical wavelength electromagnetic radiation, in particular laser radiation, and to non-linear optical (NLO) devices incorporating such materials.

It is known that various organic and inorganic compounds possess the ability to double the frequency of laser light passing through them. This ability is known as second harmonic generation (SHG) and is particularly significant because it provides the ability to produce laser light of higher energy than that provided by the initial laser light source.

Known inorganic compounds which possess SHG properties include alpha-silica, potassium dihydrogenphosphate (KDP), zinc blende wurtzite, and gadolinium and terbidium molybdates. Known organic compounds which possess SHG properties include urea, cadmium-thiourea complexes, L-argininium dihydrogen phosphate monohydrate (LAP), some siloxane and silicone polymeric liquid crystals, stilbene-containing liquid crystals, some silver containing emulsions, dipotassium tartrate hemihydrate, potassium sodium tartrate tetrahydrate, compounds having large secondary molecular susceptibilities (beta-values) such as 4-(N-pyrrolidino)-3-(N-ethanamido)-nitrobenzene (PAN) and 4-(dimethylamino)-3-(N-ethanamido)-nitrobenzene (DAN), and blends of large beta-value compounds with polypeptides as disclosed in European Patent Application Number EP-0338702-A1. A further group of materials having SHG properties is described in applicant's U.S. Pat. No. 5,352,388 and comprise a salt of an organic nitrogenous base with an optically active enantiomer of a chiral carboxylic acid, said acid containing, in addition to its carboxyl group, at least one substituent group selected from carboxyl and hydroxyl and the salt having a non-centrosymmetric crystal structure.

Within the field of known SHG materials, crystalline materials form an important class because many can be grown from solution into large, transparent single crystals of good optical quality. However, ideally a crystalline SHG material must possess a combination of desirable properties to be practically useful for incorporation in an NLO device. Amongst the most important of these properties are:—
  (1) High solubility in organic and/or aqueous media in order to promote a reasonable rate of crystal growth from solution.
  (2) Good crystal growth properties.
  (3) High thermal stability, in particular high melting point, to facilitate the (normally high temperature) incorporation of the materials into NLO devices and to provide adequate resistance to thermal damage in the presence of laser radiation.
  (4) Good mechanical strength.
  (5) Lack of colour, in order to promote high optical transmissivity at all optical wavelengths and low heat absorption of laser energy.
  (6) Absence of hygroscopy.
  (7) Ability to form hydrate-free crystals, since prolonged heating of a hydrated crystalline material by laser radiation may promote the liberation of water vapour and so degrade the structure of the material from within.
  (8) High SHG response chracteristics (should generally be superior to that of urea).
  (9) Low cost of production.

Very few crystalline materials possess a sufficient number of these properties to render them useful in practical NLO devices. The principal disadvantage of known crystalline inorganic compounds exhibiting SHG response is their generally low threshold to optical damage which leaves them vulnerable to damage by laser light. The principle disadvantages of known crystalline organic compounds exhibiting SHG response is their generally high cost of production, and their generally poor crystal strength and high volatility which results in mechanical damage and dissipation of the materials. Any material damage results in a reduction of power in the light emitted from NLO devices employing the material, and also results in the material absorbing excessive amounts of heat which can cause further damage to the material. For example, although KDP and LAP are currently widely used in NLO devices, KDP is hygroscopic, and LAP is both hydrated and possesses a melting point of only 140° C., and neither exhibits an SHG response of high magnitude. The materials disclosed for use in NLO devices in the afore-mentioned U.S. patent demonstrate an improvement over earlier SHG materials, particularly as regards their cost and effectiveness but further improvements are continuously being sought for such materials.

It is an object therefore of the present invention to provide novel materials for use in NLO devices which demonstrate enhanced properties in the areas mentioned above. It is a further object of the present invention to provide NLO devices which have enhanced performance and which incorporate the novel SHG responsive materials.

According to a first aspect of the present invention therefore there are provided materials having SHG activity which comprise those morpholinium or thiomorpholinium salts of hydroxy-substituted aliphatic or aromatic carboxylic acids selected from tartaric acid and hydroxy-substituted benzoic and cinnamic acids, which exhibit a non-centrosymmetric crystalline form. Especially preferred materials demonstrating SHG activity include the following novel salts: morpholinium 3-hydroxybenzoate, morpholinium 4-hydroxybenzoate, morpholinium 3,5-dihydroxybenzoate, morpholinium 3-fluoro-4-hydroxybenzoate, dimorpholinium 2,3,5,6-tetrafluoro-4-hydroxybenzoate, morpholinium 4-(4-hydroxyphenyl)benzoate, morpholinium tartrate and thiomorpholinium 4-hydroxybenzoate.

All of these compounds exhibit SHG activity and have generally favourable properties in respect of the various criteria discussed above. The materials morpholinium 4-hydroxybenzoate and morpholinium 3,5-dihydroxybenzoate are considered to be particularly well suited to use as SHG materials in non-linear optical devices.

As will be appreciated from the reference to dimorpholinium 2,3,5,6-tetrafluoro-4-hydroxybenzoate above, in certain instances where there are appropriate substituents on the aromatic ring, the hydroxyl substituent may also combine with the base to form a 2:1 base:acid salt and such substances—provided that they exist in a crystalline form which exhibits non-centrosymmetry—are also comprehended to be within the scope of this invention.

The present invention therefore further provides, in a second aspect, an NLO device comprising a crystalline SHG material mounted in the optical path of a laser, wherein the crystalline material is selected from the group comprising morpholinium and thiomorpholinium salts of hydroxy-substituted aliphatic or aromatic carboxylic ahcids selected from tartaric acid and hydroxy-substituted benzoic and cinnamic acids, which salts exhibit a non-centrosymmetric crystalline form. Especially preferred salts for use in such an NLO device comprise one of the novel salts listed above and more especially either morpholinium 4-hydroxybenzoate or morpholinium 3,5-dihydroxy-benzoate.

The principal advantages of using the present materials in an NLO device are that they are derived from starting materials, ie. morpholine and acids, which are both relatively inexpensive and readily available commercially. The salts themselves are easily prepared using absolute ethanol as the solvent and advantageously are transparent and colourless. They have melting points in excess of 160° C. and exhibit favourable crystal growth habits and, most importantly, good SHG performance at 1064 nm. The powder efficiency of the materials is, for example, better than that of urea which is the reference material for SHG activity.

The invention will now be further illustrated by the following examples showing the preparation of SHG materials according to this invention.

Preparation of Novel Salts

EXAMPLE 1

Preparation of Morpholinium 3-hydroxybenzoate (M3)

In a conical flask, cold absolute ethanol (ca. 40 ml) was added to 99% pure 3-hydroxybenzoic acid (1.8495 g; 13.39 mmol). Dissolution of the acid was achieved at room temperature by constant stirring. Morpholine (1.1653 g, 13.39 mmol) was added dropwise to the acid solution. The reaction was exothermic and some white fumes were observed; the turbid white solution of the acid turned yellow on addition of the colourless morpholine. The opening of the conical flask was covered with parafilm which was then punctured to allow slow evaporation of the solvent at room temperature. Transparent white polyhedral crystals of morpholinium 3-hydroxybenzoate were formed within 24 hrs. The crystals were filtered and washed with small aliquots of cold ethanol. Yield >70% (not optimised).

C:H:N:—Found C, 58.8%; H, 6.8%; N, 6.2%. Calculated for 1:1 salt:—C, 58.7%; H, 6.7%; N, 6.2%. Melting point: 141.8° C. Space Group Cc (No. 9)

EXAMPLE 2

Preparation of Morpholinium 4-hydroxybenzoate (M4)

In a conical flask, cold absolute ethanol (ca. 50 ml) was added to 4-hydroxybenzoic acid (2.4559 g; 17.78 mmol). Dissolution took place on heating the solution on a hot plate with stirring to a maximum of 78° C. To the cooled (unfiltered) colourless solution morpholine (1.5491 g; 17.78 mmol) was added dropwise by pipette. The reaction was exothermic with an increase in temperature of ca. 15° C. on addition of the morpholine; emission of some white fumes and a slight yellowing of the acid solution occurred. Immediate precipitation of morpholinium 4-hydroxybenzoate in white powdered form occurred. The powder was collected by filtration, dissolved in the minimum of boiling ethanol to give a colourless solution and filtered. The conical flask containing the hot solution was sealed with parafilm and surrounded in aluminium foil. White transparent rhombic plates were afforded within 1 hr. of slow evaporation of the solvent at room temperature. Yield >85% (not optimised).

C:H:N:—Found C, 58.7%; H, 6.8%; N, 6.2%. Calculated for 1:1 salt C, 58.7%; H, 6.7%; N, 6.2%. Melting point: 186.7° C. Spacegroup Cc (No. 9). SHG activity was better than for urea.

EXAMPLE 3

Preparation of Morpholinium 3,5-dihydroxybenzoate (M35)

In a conical flask, covered with aluminium foil, cold absolute ethanol (ca. 50 ml) was added to 3,5-dihydroxybenzoic acid (2.7056 g; 19.62 mmol). Dissolution took place on heating the solution on a hot plate with stirring to a maximum of 78° C. To the cooled, slightly beige solution morpholine (1.5294 g; 19.62 mmol) was added dropwise by pipette. The reaction was exothermic with an increase in temperature of ca. 10° C. on addition of the morpholine; the emission of some white fumes and a slight yellowing of the acid solution occurred. The conical flask was kept cool at ~5° C. and precipitation of morpholinium 3,5-dihydroxybenzoate as off-white powdered form occurred within 48 hrs. of reaction. The powder was collected by filtration, and recrystallised (dark) from a minimum volume of hot isopropyl alcohol: water (10:1) mixture to give hedgehog-type clusters of transparent off-white plates. Yield >85% (not optimised).

C:H:N:—Found C, 54.7%; H, 6.3%; N, 5.8%. Calculated for 1:1 salt C, 54.8%; H, 6.3%; N, 5.8%. Melting point: 218.3° C. Space Group $Pna2_1$ (No. 33).

EXAMPLE 4

Preparation of Morpholinium Tartrate (Mtart)

Cold absolute ethanol (ca. 60 ml) was added to L-tartaric acid (2.9451 g; 19.62 mmol) in a conical flask. The acid was dissolved by heating the mixture on a hot plate with stirring to ca. 78° C. The colourless solution was cooled to below 30° C. and morpholine (1.7095 g; 19.62 mmol) was added dropwise by pipette. No discoloration of the acid solution occurred, The product morpholinium tartrate precipitated out of the solution immediately as a white powder. The product was collected by vacuum filtration and recrystallized from boiling ethanol. The resulting flaky thin plates were unsuitable for single crystal x-ray diffraction. The flaky crystals were recrystallized from boiling methanol to yield white transparent trapezia suitable for x-ray analysis. Yield >85% (not optimised).

C:H:N:—Found C, 40.4%; H, 6.4%; N, 5.8%. Calculated for 1:1 salt C, 40.5%; H, 6.4%; N, 5.9%. Melting point: 170.6° C. Spacegroup $P2_12_12_1$ (No. 19). SHG activity was similar to that of ADP.

EXAMPLE 5

Preparation of dimorpholinium 2,3,5,6-tetrafluoro-4-hydroxybenzoate (M24F4)

In a conical flask, cold absolute ethanol (ca. 40 ml) was added to 2,3,5,6-tetrafluoro-4-hydroxybenzoic acid (3.839 g; 16.83 mmol). The acid was dissolved by heating on a hot plate with stirring. To the cooled, colourless solution morpholine, in double the molar ratio (2.9324 g; 33.67 mmol), was added dropwise by pipette. The solution remained colourless. The conical flask was covered in punctured parafilm and the solvent was allowed to evaporate at room temperature. After 1 hr the product dimorpholinium 2,3,5,6-tetrafluoro-4-hydroxybenzoate had precipitated out as a microcrystalline powder. Recrystallisation of the powder from boiling ethanol afforded small transparent white cube-type crystals. Yield >80% (not optimised).

C:H:N:—Found C, 46.6%; H, 5.1%; N, 7.2%. Calculated for 2:1 base:acid salt C, 46.9%; H, 5.3%; N, 7.3%. Melting point: 155.0° C. Spacegroup Cc (No. 9). The SHG activity for this material was weaker than that of urea but better than for ADP.

EXAMPLE 6

Preparation of Morpholinium 3-fluoro-4-hydroxybenzoate (M3F4)

Cold absolute ethanol (ca. 20 ml) was added to 3-fluoro-4-hydroxybenzoic acid (0.4203 g; 2.69 mmol). The solution was heated to aid dissolution. Morpholine (0.2346 ml; 2.69 mmol) was added dropwise to the cooled beige solution of the acid. No colour change to the acid solution occurred. The solvent was allowed to evaporate slowly at room temperature. The product morpholinium 3-fluoro-4-hydroxybenzoate precipitated out of solution within 48 hr as a beige powder. Recrystallization of the powder from the minimum of boiling ethanol afforded very flaky off-white plates. The crystals were not suitable for single crystal x-ray diffraction. Yield >85% (not optimised).

C:H:N:—Found C, 54.3%; H, 5.8%; N, 5.7%. Calculated for 1:1 salt C, 54.3%; H, 5.8%; N, 5.8%. Melting point: 186.7° C. SHG activity slightly weaker than that of urea.

EXAMPLE 7

Preparation of Morpholinium 4-(4-hydroxyphenyl)benzoate (M4long)

Absolute ethanol (ca. 40 ml) was added to 4-(4-hydroxyphenyl)benzoic acid (1.4092 g; 6.58 mmol). The mixture was heated to complete dissolution. The colourless solution was allowed to cool to below 30° C. and morpholine (0.573 g; 6.58 mmol) was added dropwise. No exothermicity or discoloration of the acid solution was observed on addition of the base. The solvent was allowed to evaporate slowly at room temperature. Within 48 hr the product morpholinium 4-(4-hydroxyphenyl)benzoate had crystallised out of solution as elongated transparent white rectangular plates. Yield >85% (not optimised).

C;H;N:—Found C, 68.1%; H, 6.5%; N, 4.7% Calculated for 1:1 salt C, 67.8%; H, 6.4%; N, 4.7%. Melting point: 212.4° C. Spacegroup $P2_12_12_1$ (No. 19). SHG activity is similar to that of urea.

EXAMPLE 8

Preparation of Morpholinium 4-hydroxycinnamate (M4HCA)

In a 500 ml conical flask cold absolute ethanol (ca. 200 ml) was added to 4-hydroxy cinnamic acid (12.1018 g, 73.72 mmol) to give a pale yellow solution. (Cold ethanol was used since a darkening of the acid solution was observed when hot ethanol was used. This is possibly due to slow oxidation of the double bond of the acid in solution, the rate of which is increased by heating).

Morpholine (6.4224 g, 73.72 mmol) was added to the solution of 4-hydroxycinnamic acid in ethanol slowly by pipette while stirring the solution. A slight darkening of the pale yellow acid solution was observed on addition of the morpholine. The reaction was mildly exothermic. The conical flask was covered in parafilm which was punctured to allow slow evaporation of the solvent. The solution was placed in the refrigerator and transparent white thin conglomerated plates of morpholinium 4-hydroxycinnamate were formed within 72 hours. The crystals were isolate by vacuum filtration and washed with small aliquots of cold ethanol. Yield >70% (not optimised).

C;H;N:—Found C, 62.3%; H, 6.8%; N, 5.5% Calculated for 1:1 salt $(C_{13}H_{17}O_4N)C$ 62.1%; H, 6.8%; N, 5.6%. Melting point: 179.7° C. Spacegroup Cc (No. 9). SHG activity is greater than that of urea.

EXAMPLE 9

Preparation of thiomorpholinium 4-hydroxybenzoate (TM4)

In a conical flask, cold absolute ethanol (ca. 100 ml) was added to 4-hydroxybenzoic acid (5.4932 g; 39.77 mmol). The mixture was heated to afford complete dissolution. Thiomorpholine (4.104 g; 33.77 mmol) was added to the cooled acid solution. The thiomorpholine, which was dark yellow, caused the solution of acid to assume a yellow colouration. No white fumes were observed unlike those observed during the reaction of morpholine and 4-hydroxybenzoic acid. The reaction was mildly exothermic. Immediate precipitation of the product thiomorpholinium 4-hydroxybenzoate as a white powder occurred. The powder was collected by vacuum filtration, washed with cold ethanol then recrystallized from boiling ethanol. Two polymorphs of the 1:1 salt have been isolated: white transparent cube-type crystals of the compound in a centrosymmetric space group $P2_1/c$ (No. 14) and white transparent elongated plates of the same 1:1 salt in the noncentrosymmetric space group Cc (No. 9). In some batches of the compound preferential crystallisation of the Cc polymorph occurred after two recrystallizations of the salt in boiling ethanol. However, this noncentrosymmetric polymorph has proved to be unstable, with the crystals becoming opaque over time (even if sealed in a container). Yield (combined polymorphs)>85% (not optimised).

C:H:N (centrosymmetric polymorph):—Found C, 54.3%; H, 6.3%; N, 5.9% Calculated for 1:1 salt: C, 54.8%; H, 6.3%; N, 5.8%. Melting points: 165.6° C. (noncentrosymmetric polymorph), 191.2° C. (centrosymmetric polymorph). Spacegroup $C_c$ for the non-centrosymmetric form. SHG activity is slightly better than for ADP.

EXAMPLE 10

Preparation of thiomorpholinium 3,5-dihydroxybenzoate (TM35)

Absolute ethanol (ca. 40 ml) was added to 3,5-dihydroxybenzoic acid (2.298 g; 14.91 mmol) in a conical flask. The mixture was heated to complete the dissolution. Thiomorpholine (1.539 g: 14.91 mmol) was added dropwise to the cooled pale beige solution of the acid. Addition of the dark yellow base to the acid resulted in a bright greenish yellow coloration. The reaction was only mildly exothermic unlike that between morpholine and 3,5-dihydroxybenzoic acid. Precipitation of a beige powder occurred after 24 hrs. Recrystallization of the compound yielded a beige microcrystalline powder and some small rectangular plates. Analysis of the crystal structure revealed the plates to be thiomorpholinium 3,5-dihydroxybenzoate in the centrosymmetric polymorph C2/c. Further recrystallization of the compound afforded beige hexagonal plates which were found to be the 1:1 salt in the non-centrosymmetric space group $P2_12_12_1$ (No. 19). Yield (combined polymorphs)>70% (not optimised).

C:H:N:—(initial powder) Found C, 51.4%; H, 6.0%; N, 5.1% Calculated for 1:1 salt C, 51.5%; H, 5.9%; N, 5.4%. Melting point: 180.2° C. (centrosymmetric polymorph); 184.9° C. (non-centrosymmetric polymorph). SHG activity is slightly better than for urea.

SHG Performance

Samples of all of the materials prepared as described above were first subjected to an initial screening with the results shown in Table 1. For this examination ungraded (as to size) powdered samples of each material were sandwiched between two glass plates which were then held in the path of a pulsed Nd:YAG laser operating at 1064 nm. (Model SL804 from Spectron Laser Systems Ltd). The SHG response was judged by viewing the intensity of green light generated (viewed through laser goggles which passed green light but stopped the fundamental 1064 nm radiation). The SHG activity was qualitatively compared to that of a reference sample which was either ungraded urea or ammonium dihydrogen phosphate (ADP).

TABLE 1

Initial Screening of Products

| Example | Sample reference | Appearance | SHG Response |
|---|---|---|---|
| 1 | M3 | Polyhedra, transparent white | slightly weaker than urea |
| 2 | M4 | Polyhedra, white | better than urea |
| 3 | M35 | Polyhedra, white | slightly better than urea |
| 4 | MTart | White, transparent trapezia | similar to ADP |
| 5 | M24F4 | White, transparent crystals | better than ADP, weaker than urea |
| 6 | M3F4 | Off-white plates | slightly weaker than urea |
| 7 | M4long | Rectangular plates, transparent | similar to urea |
| 8 | M4HCA | White plates, transparent | better than urea |
| 9 | TM4 | Off-white powder | slightly better than ADP |
| 10 | TM35 | Beige hexagonal plates | slightly better than urea |

Assessment of Phase Matching Properties.

The phase matching properties of those more promising materials which performed well in the initial screening have been evaluated using the well established Kurtz and Perry technique (*J Appl Phys*, 1968, 39, 3798). In this method the SHG intensity ($\lambda$=532 nm) is measured as a function of the particle size for a fixed input pulse energy. In phase matching materials, a particular direction exists in which both the fundamental wave (frequency $\omega$) and the second harmonic wave (frequency $2\omega$) travel in phase through the material. The consequence of this is that the harmonic fields can build up in amplitude thus making the material more desirable for SHG applications.

To perform the Kurtz and Perry test powdered samples of the materials were graded using a mechanical shaker set up with a set of standard sieves (550 μm to 40 μm). The graded powders were then mounted in a thin aluminium holder placed between two glass slides. The following criteria was used to ensure the validity of the method:

$$r<L<D$$

where, r=average particle size
L=thickness of the powdered sample (i.e. thickness of the aluminium spacer)
D=diameter of the laser beam incident on the sample.

In the present experiments, there was at least an order of magnitude difference between these parameters.

The same laser as before was used to provide 12 ns FWHM pulses at 1064 nm. The energy of the input pulse was directly measured using a Scientech AD30 energy meter employing a calorimetric detector type AC2501H, supplied by Scientech. The magnitude of the SHG signal was measured as the number of counts using an Optical Multichannel Analyser (OMA) with an intensified array. This was preferred to a photomultiplier tube as it enabled the presence of any fluorescence or abnormal spectral emissions from the sample, for example due to damage etc., to be determined.

Materials M3, M4 and M35 were selected for testing by the above-described method and the results of these tests showed that the SHG signal level does not decrease for increasing particle size. This is an indication of phase matching condition.

The experimental set-up was validated by measurements on two standards: urea (organic standard) and an inorganic standard, ADP. Both were found to be phase matching materials. This result is consistent with the published data.

Crystal Growth a) Equipment

Crystals of M4, M35 and M3 were grown from solution by lowering the temperature of the saturated solutions. The crystal growth equipment consists of a heated tank of water into which the vessel containing the saturated solution of the material is held. The glass tank is heated through a UV block filter by an infra-red lamp. The temperature is controlled by a mercury contact thermometer. The glass tank is covered by aluminium foil to exclude UV in sunlight from entering the glass tank.

b) Growth of M4 crystals.

Crystals of M4 have been grown using the equipment described above, both from ethanol and IPA by reduction of temperature of the saturated solutions (12 g of M4 in 820 ml of ethanol) from 40° C. to 25° C. A seed crystal, which had been previously washed with a solvent was suspended from a stirrer and carefully introduced into the saturated solution. After a short equilibration period, during which the seed was observed for any signs of dissolution, the temperature of the tank was set to reduce. Several temperature decay rates were tried. A decay of −0.5° C. per 24 hr was found to give the best results. In a typical run, a crystal of M4 20 mm×15 mm×6 mm was grown in 16 days. The weight of the crystal was 1.9 g. The growth run was accompanied by precipitation of multiple seeds. Ethanol grown crystals are the largest, typically 15 mm×10 mm×4 mm. IPA grown crystals are smaller, mainly due to the fact that M4 is less soluble in IPA.

Crystals grown from IPA and ethanol both show high SHG activity.

c) Growth of M35 Crystals

The solubility of M35 has been determined in isopropyl alcohol/water (10:1 ratio) mixture over a temperature range of 5° C. to 40° C. Crystal growth attempts using decay rates of −0.25° C. per 24 hr have yielded a good stock of small triangular shaped crystals with typical dimensions of approximately 2 mm×2 mm×1 mm. One of these crystals was used as a seed to grow a larger crystal approximately 5 mm×5 mm×5 mm in size. A part of this crystal (defective region) was removed and the resulting section was used as a seed to grow a crystal that was approximately 4 mm×3 mm×2 mm in size. The quality of this crystal was sufficiently good to demonstrate high SHG activity.

The transmission spectrum of a single crystal of M35 exhibits optical transparency down to 350 mm. The crystals of M35, once removed from the growing solution are stable and do not show any deterioration in quality. The optical quality could be improved by better stirring.

d) Growth of M3 Crystals

M3 has as yet only been grown as small seed crystals. These have been shown to exhibit SHG activity.

Doubling into the Blue

Experimental

The capability for novel materials of the invention to achieve frequency doubling into the blue area of the spectrum was examined. The light source for this investigation was a MOPO (Master Oscillator Power Oscillator) model 730-10 pumped by GCR 270-10 Nd:YAG laser (supplied by Spectra Physics). The incident pulse width output from this laser ranged from 4 ns to 6 ns. Light of a specified wavelength was directed onto a sample sandwiched between two plates in a sample holder. In order to determine the energy which was incident on a sample for each test wavelength, the sample holder was movable in and out of the light beam and an energy meter was located behind the sample position so that the light beam would be directed onto the meter when a sample was not in position. The test wavelengths used were 950 nm, 850 nm, 800 nm and 780 nm. The energy meter was a Scientech AD30 meter employing a calorimetric detector type AC2501H supplied by Scientech.

Results

Samples of the M4, M3 and M35 materials were tested for frequency doubling effect at each of the test wavelengths, the performance of each sample being judged qualitatively by eye by examination of the frequency doubled radiation scattered from the sample. These qualatative assessments were compared with that of a similarly prepared sample of urea having the same particle size as the materials of the invention. The results obtained are set out in Table 2. The M3 and M4 samples were ungraded while the M35 sample was a 212–300 µm graded sample.

TABLE 2

| | Frequency Doubling into the blue | | | |
|---|---|---|---|---|
| Wavelength (nm) | Energy (mJ) | M4 | M3 | M35 |
| 950 | 9 | Better | Slightly less | same or better |
| 850 | 12.3 | Slightly less | Less | same or better |
| 800 | 14.8 | Slightly less | Much less | slightly less |
| 780 | 16.7 | Slightly less | Less | better |

The above results indicate that these materials could provide crystalline samples capable of frequency doubling into the blue with high efficiency. Phase matching is indicated due to the relatively large particle sizes used in both the graded (M35) and ungraded samples (M4 and M3) used.

The invention claimed is:

1. A material having SHG activity which comprises a morpholinium or thiomorpholinium salt of a hydroxy-substituted aliphatic or aromatic carboxylic acid selected from tartaric acid and hydroxy-substituted benzoic and cinnamic acids, which salt exhibits a non-centrosymmetric crystalline form.

2. A material as claimed in claim 1 selected from the group comprising morpholinium 3-hydroxybenzoate, morpholinium 4-hydroxybenzoate, morpholinium 3,5-dihydroxybenzoate, morpholinium 3-fluoro-4-hydroxybenzoate, dimorpholinium 2,3,5,6-tetrafluoro-4-hydroxybenzoate, morpholinium 4-(4-hydroxyphenyl)benzoate, morpholinium tartrate, morpholinium 4-hydroxycinnamate, thiomorpholinium 4-hydroxybenzoate and thiomorpholinium 3,5-dihydroxybenzoate.

3. A non-linear optical device comprising a crystalline SHG material mounted in the optical path of a laser, wherein the crystalline material is comprised of a material as claimed in claim 1.

4. A non-linear optical device as claimed in claim 3 wherein the crystalline material is comprised of either morpholinium 4-hydroxybenzoate or morpholinium 3,5-hydroxybenzoate.

* * * * *